US012453643B2

(12) United States Patent
Kiska et al.

(10) Patent No.: US 12,453,643 B2
(45) Date of Patent: Oct. 28, 2025

(54) IMPLANT EXTRACTOR

(71) Applicant: Shukla Medical, St. Petersburg, FL (US)

(72) Inventors: Mitchell Ryan Kiska, Seminole, FL (US); Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 518 days.

(21) Appl. No.: 17/852,844

(22) Filed: Jun. 29, 2022

(65) Prior Publication Data

US 2023/0000644 A1 Jan. 5, 2023

Related U.S. Application Data

(60) Provisional application No. 63/217,876, filed on Jul. 2, 2021.

(51) Int. Cl.
*A61F 2/46* (2006.01)

(52) U.S. Cl.
CPC .... *A61F 2/4603* (2013.01); *A61F 2002/4619* (2013.01); *A61F 2002/4628* (2013.01)

(58) Field of Classification Search
CPC .................. A61F 2/4607; A61F 2/4603; A61F 2002/4619
See application file for complete search history.

(56) References Cited

U.S. PATENT DOCUMENTS

| | | | | |
|---|---|---|---|---|
| 5,534,006 | A * | 7/1996 | Szabo | A61F 2/4607 606/100 |
| 8,603,100 | B2 | 12/2013 | Muller | |
| 9,924,754 | B1 | 3/2018 | Soto et al. | |
| 10,912,656 | B2 | 2/2021 | Müller | |
| 11,617,660 | B2 * | 4/2023 | Alden | A61F 2/4607 606/99 |
| 11,622,869 | B2 * | 4/2023 | Alden | A61F 2/4607 606/99 |
| 11,779,468 | B2 * | 10/2023 | Keach | A61B 17/921 606/99 |
| 2008/0221576 | A1 * | 9/2008 | Keller | A61F 2/4607 606/151 |

(Continued)

FOREIGN PATENT DOCUMENTS

DE 202018103170 U1 6/2018

OTHER PUBLICATIONS

Extended European Search Report in counterpart European Patent Application No. 22182653.0, mailed Oct. 6, 2022.

(Continued)

*Primary Examiner* — David W Bates
(74) *Attorney, Agent, or Firm* — Kim IP Law Group LLC

(57) ABSTRACT

An implant extractor for use in orthopedic surgeries. The implant extractor provides a line of force substantially parallel to an implant to be extracted. The implant extractor includes a curved body having a curved jaw track configured to slidingly receive a correspondingly curved jaw for clamping a trunnion of an implant, e.g., a hip stem implant. A push rod urges the curved jaw into clamping engagement with the trunnion under the influence of a cam handle having a continuously curved cam surface.

16 Claims, 23 Drawing Sheets

(56) References Cited

U.S. PATENT DOCUMENTS

| | | | | |
|---|---|---|---|---|
| 2008/0262503 | A1* | 10/2008 | Muller | A61F 2/4612 606/99 |
| 2014/0207123 | A1* | 7/2014 | Mueller | A61F 2/4607 606/1 |
| 2016/0059403 | A1* | 3/2016 | Mugnier | A61B 17/14 16/422 |
| 2018/0042734 | A1* | 2/2018 | Slater | A61F 2/4607 |
| 2019/0374349 | A1* | 12/2019 | Müller | A61F 2/4607 |
| 2021/0315713 | A1* | 10/2021 | Keach | A61B 17/92 |

OTHER PUBLICATIONS

Ganter Norm: "Normelemente Katalog", p. 675, Jun. 1, 2021, Retrieved from the Internet: URL:https://www.ganternorm.com/fileadmin/user_upload/downloads/kataloge/katalog_18_0.pdf.

SEA-DOO 947 951 DI Exhaust Manifold Wrench, ritcoproducts.com, [online], [site visited May 11, 2023], Available from internet , URL: https ://ritcoproducts .com/products/sea-doo-947-951-di-exhaust-manifold-wrench-3d-gtx-xp-gsx-l-xp-l-rv-sportster (Year: 2023).

Nibbler Metal Cutter Sheet, amazon.com, first available Jul. 24, 2020 [online], [site visited May 11, 2023], Available from internet, URL: https ://www.amazon.com/Double-Adj ustable-N ibbler-Electric-Cutti ng/dp/B08D KTFCLD (Year: 2020).

Cam Handle with 1⅜" Screw Holes, reflectwindow.com, [online], [site visited May 11, 2023], Available from internet, URL: https: //www.reflectwindow.com/products/cam-handle-with-1-3-8-screw-holes (Year: 2023).

Pole Operated Cam Handle, windowhardwaredirect.com, [online], [site visited May 11, 2023], Available from internet, URL: https: //windowhardwaredirect.com/products/pole-operated-cam-handle-left-or-right-hand-sold-separately (Year: 2023).

WRS Project-Out Handle With Pole Hole, windowhardwaredirect.com, [online], [site visited May 11, 2023], Available from internet, URL: https ://wi ndowhardwaredi rect.com/products/wrs-project-out-handle-with-pole-hole-white-bronze-left-and-right-hand-sold-separately (Year: 2023).

Stainless Pole Operated Right Hand Cam Handle, reflectwindow.com, [online], [site visited May 11, 2023], Available from internet, URL : https://www.reflectwindow.com/products/stainless-pole-operated-right-hand-cam-handle (Year: 2023).

Bent Hohmann Retractors, Narrow, Long Handle, mprortho.com, [online], [site visited May 11, 2023], Available from internet, URL: https://mprortho.com/product/bent-hohmann-retractors-narrow-2/ (Year: 2023).

European Patent Office, Examination Report in counterpart application No. 22182653.0 mailed on Oct. 2, 2024.

* cited by examiner

IMPLANT EXTRACTOR

CROSS-REFERENCE TO RELATED APPLICATION(S)

This application claims the benefit under 35 U.S.C. § 119(e) to U.S. Provisional Application No. 63/217,876, filed Jul. 2, 2021, the entire disclosure of which is hereby incorporated by reference for all purposes.

BACKGROUND OF THE DISCLOSURE

Typical hip stem implant extractor tools employ a posterior or posterior-lateral approach to extracting a hip stem implant. A posterior or posterior-lateral approach suffers from practical disadvantages, thereby rendering the procedure less than optimum.

BRIEF SUMMARY OF THE DISCLOSURE

In accordance with an exemplary embodiment there is provided an implant extractor comprising a shaft body and a push rod extending from the shaft body. A curved jaw support arm extends from the shaft body, and a curved jaw is slidable along the curved jaw support arm and movable between a locking position and an unlocking position.

According to an aspect, the push rod is housed within the shaft body and movable relative to the shaft body. According to another aspect, a distal end of the push rod engages a proximal end of the curved jaw. According to another aspect, the curved jaw support arm has a radius of curvature of about 5 to 21 mm. According to another aspect, a distal end of the curved jaw support arm includes a central passageway having a longitudinal axis transverse to a longitudinal axis of the shaft body.

According to an aspect, the implant extractor further comprises a gripping insert received within the central passageway at the distal end of the curved jaw support arm. According to another aspect, the gripping insert includes grip enhancing structure that aligns with the curved jaw when the gripping insert is received within the central passageway. According to another aspect, the gripping insert is annular with a lateral opening for receiving the curved jaw.

According to an aspect, the implant extractor further comprises a cam lock operatively engaged with the push rod. According to another aspect, the cam lock includes a cam housed within the shaft body, and a lever extending from the cam. According to another aspect, the cam lock includes a cam having a continuously curved cam surface throughout its range of motion. According to another aspect, the continuously curved cam surface includes a first portion with a continuously increasing radius of curvature contiguous with a second portion with a continuously decreasing radius of curvature, wherein a juncture of the first portion and the second portion defines a locking portion of the continuously curved cam surface. According to another aspect, the first portion and the second portion are each convex in shape. According to another aspect, the locking portion is convex in shape and has no ridge-shaped profile.

According to an aspect, the implant extractor further comprises a tool connector extending from a proximal end of the shaft body.

In accordance with another exemplary embodiment there is provided an implant extractor comprising a shaft body and a tool connecter extending from a proximal end of the shaft body. A push rod is mounted within and is slidable within the shaft body. A cam lock is mounted within the shaft body for engaging a proximal end of the push rod. A curved jaw support arm extends from the shaft body, and a curved jaw is slidable received in the curved jaw support arm and is movable between a locking position and an unlocking position.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1:
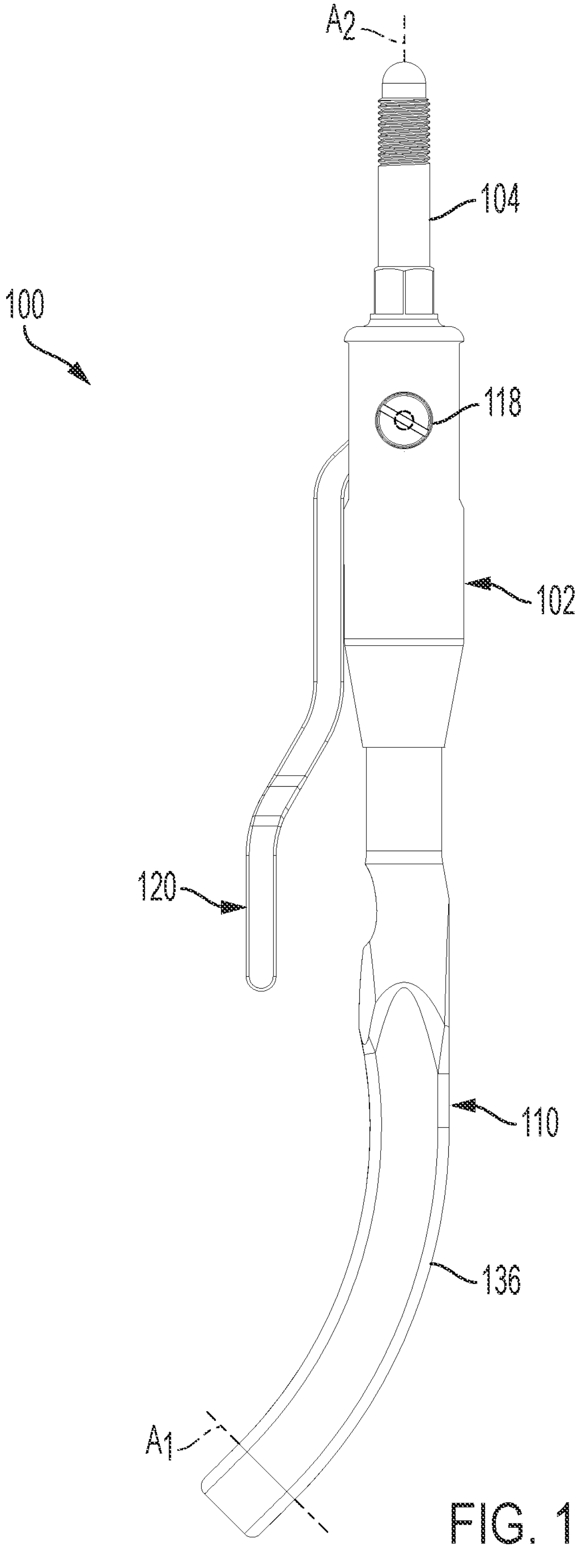
FIG. 1 is side view of an implant extractor in accordance with an exemplary embodiment of the subject disclosure.
Figure 2:
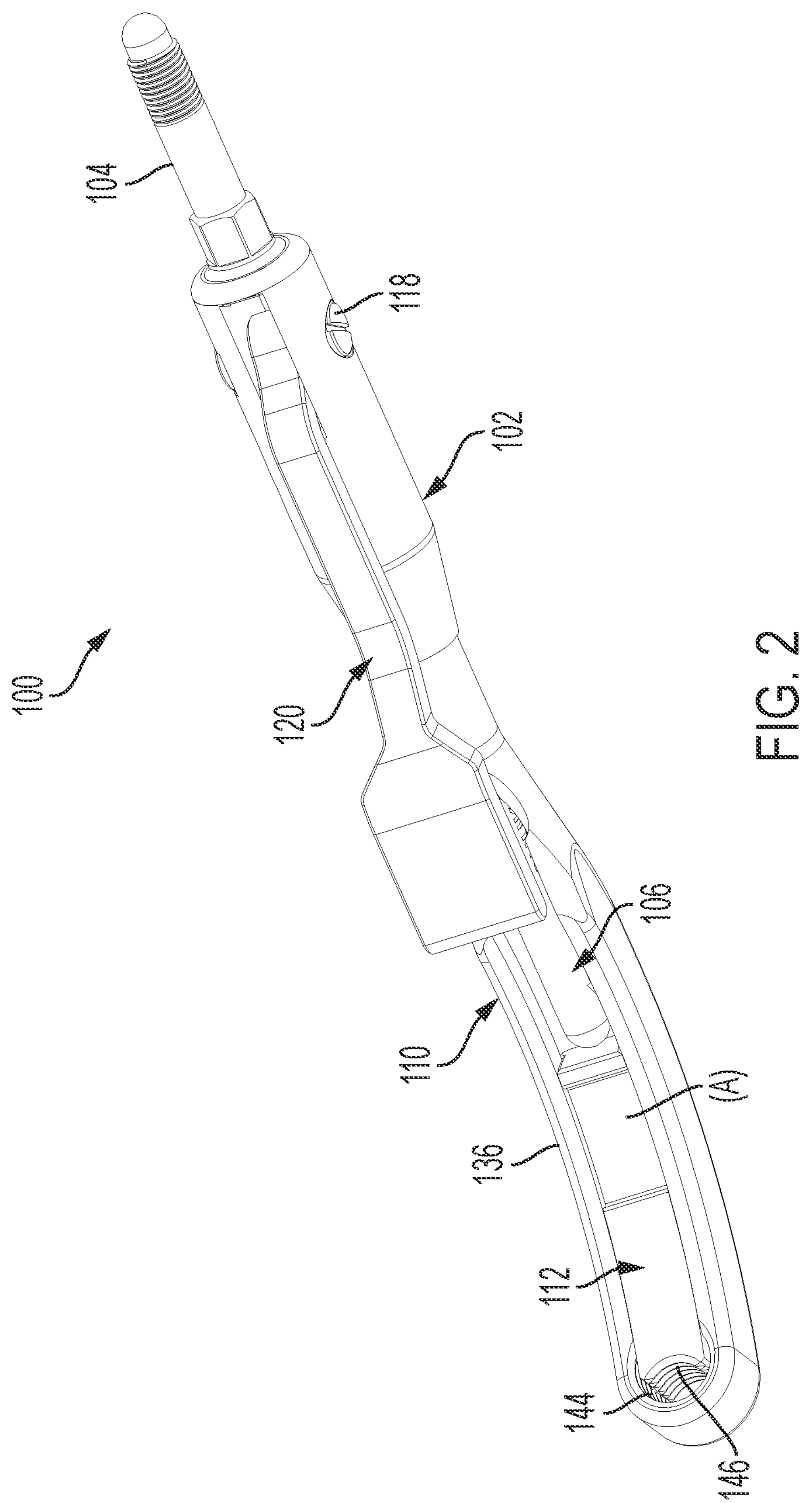
FIG. 2 is a perspective view of the implant extractor of FIG. 1
Figure 3:
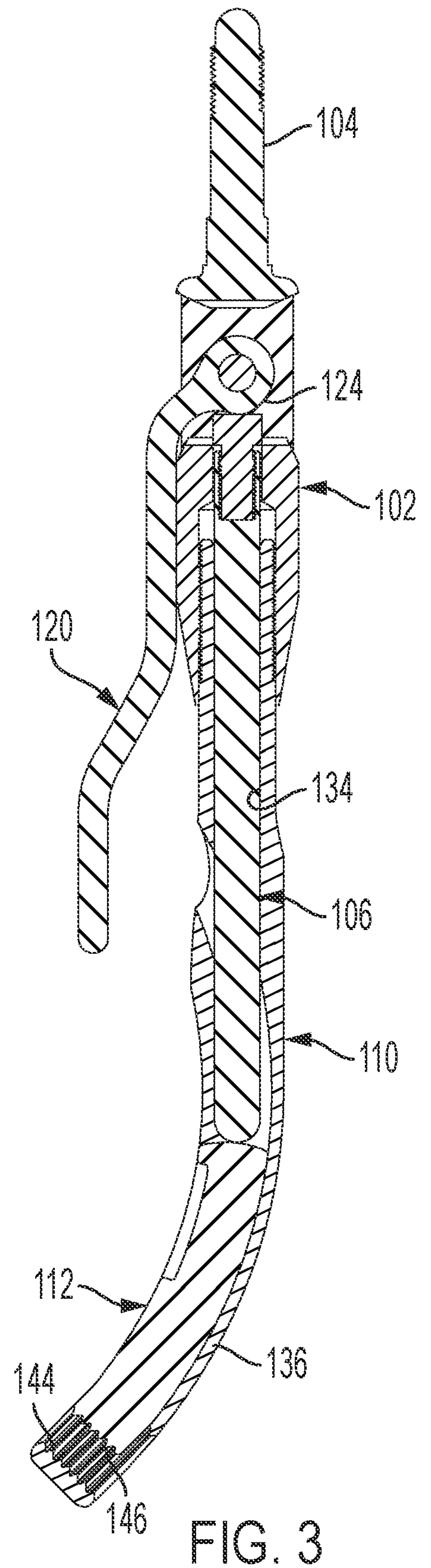
FIG. 3 is a side cross-sectional view of the implant extractor of FIG. 1.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

The exemplary embodiments of present invention relate generally to a surgical extraction tool, and more specifically, to a tool for extracting an implant from bone including, without limitation, a hip stem implant.

Figure 18:
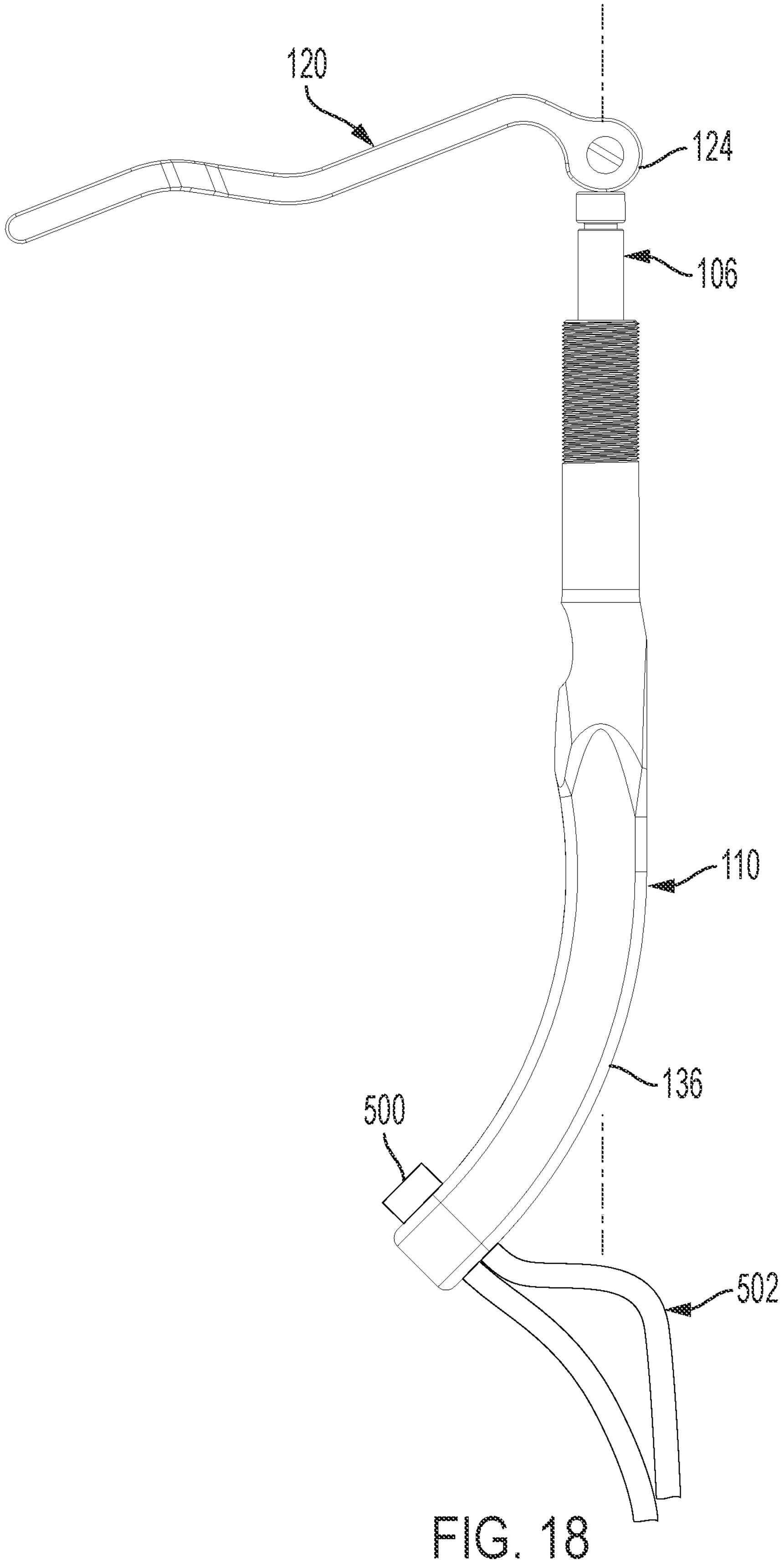
FIG. 18 is a side view of a portion of the implant extractor of FIG. 1 engaged with a trunnion of an implant and with the cam lock thereof shown in a non-camming position.
Figure 19:
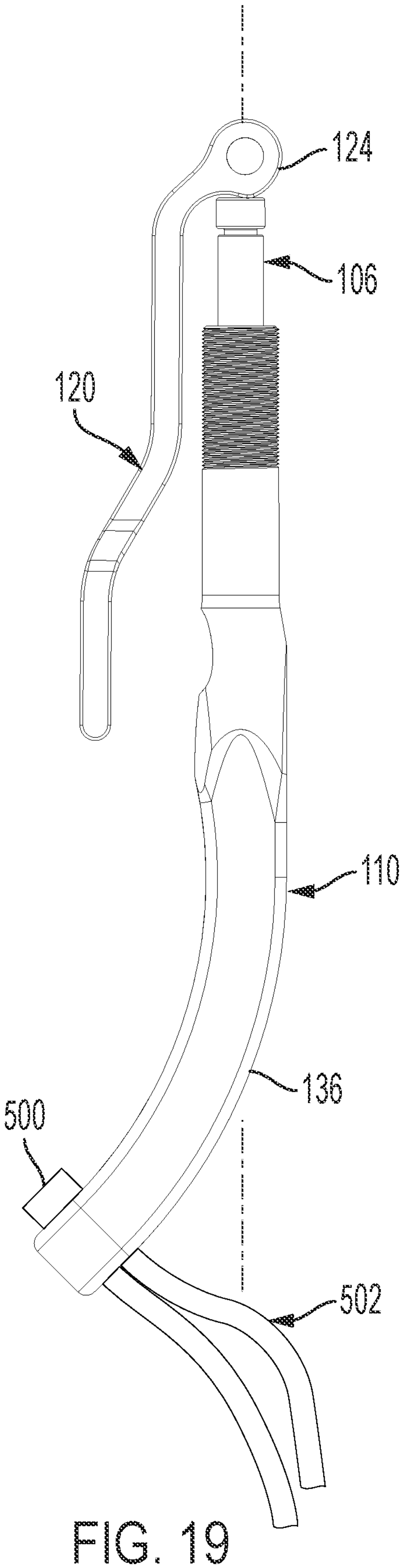
FIG. 19 is a view similar to FIG. 18 with the cam lock shown in a camming position.
Figure 20:
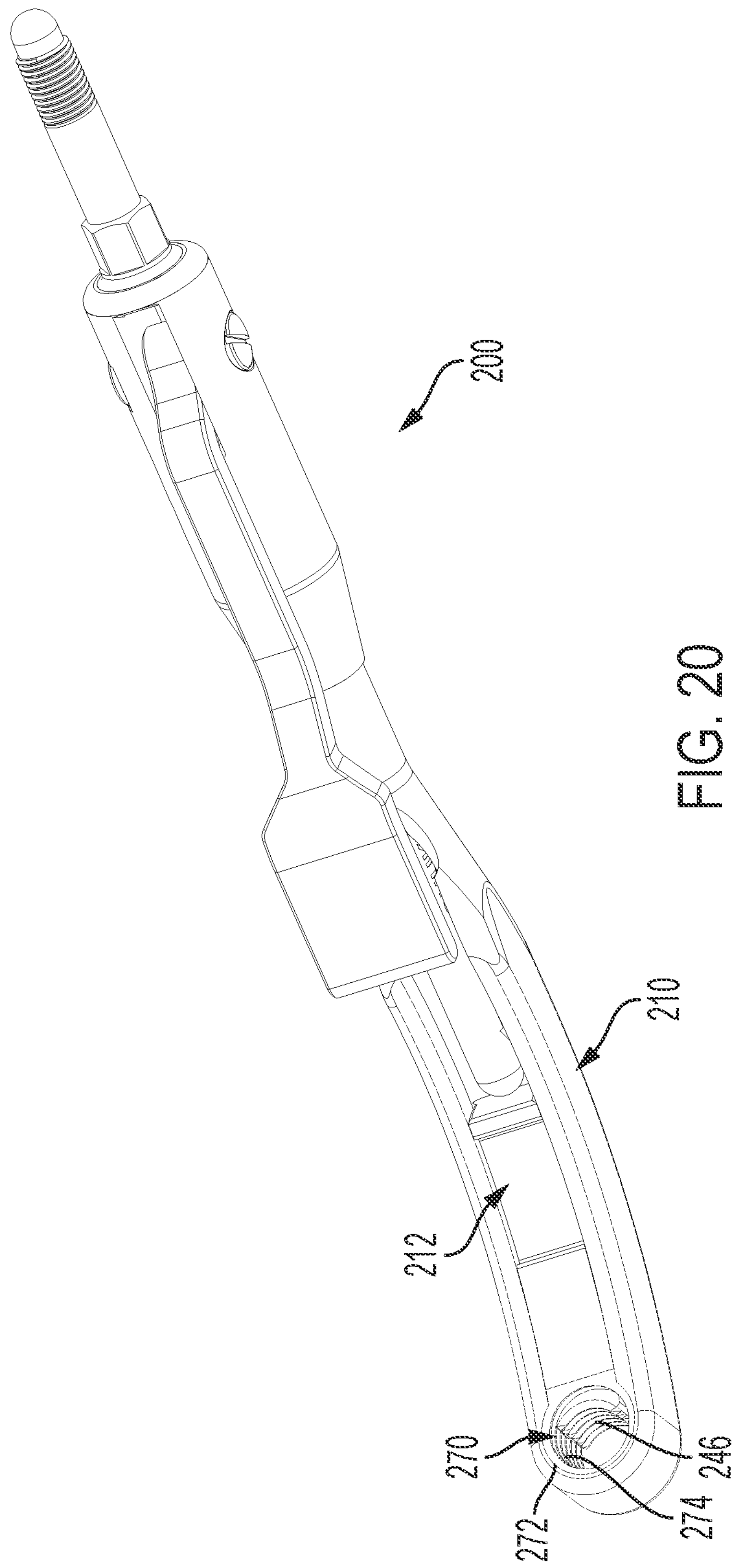
FIG. 20 is a perspective view of an implant extractor in accordance with another exemplary embodiment of the subject disclosure.
Figure 21:
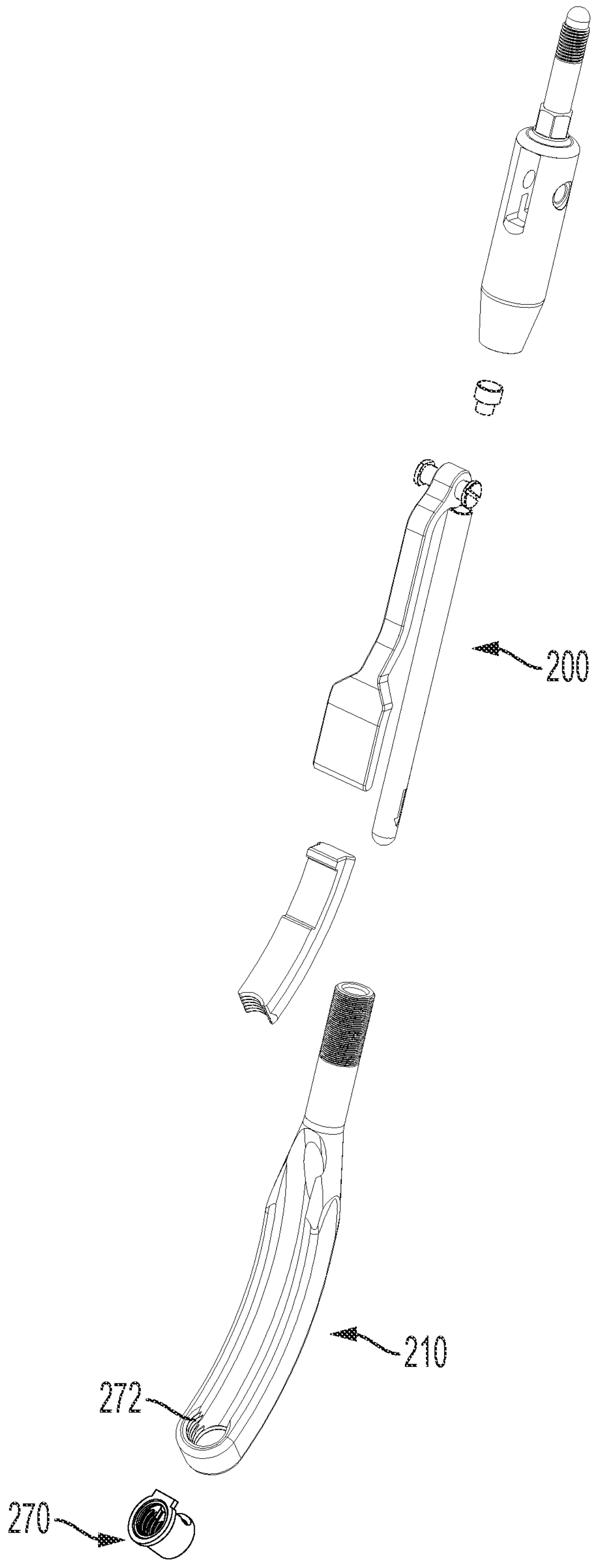
FIG. 21 is an exploded view of the implant extractor of FIG. 20.
Figure 22:
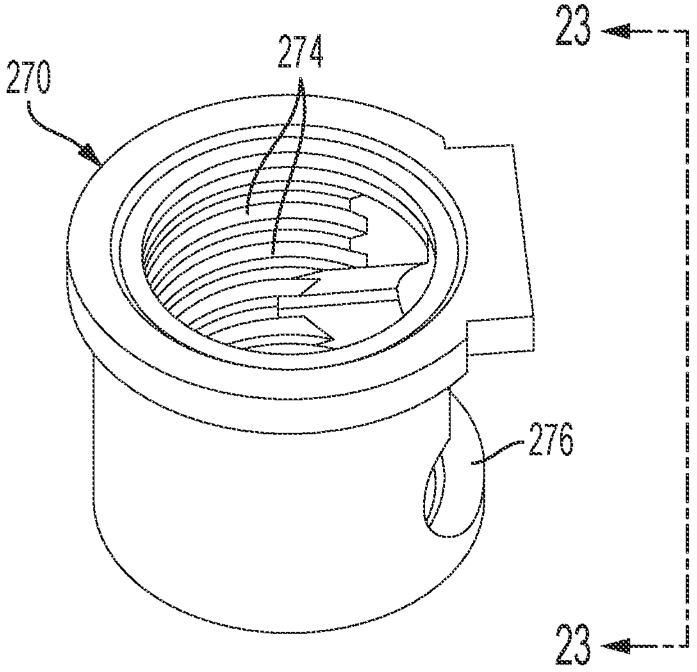
FIG. 22 is a perspective view of a gripping insert of the implant extractor of FIG. 20.
Figure 23:
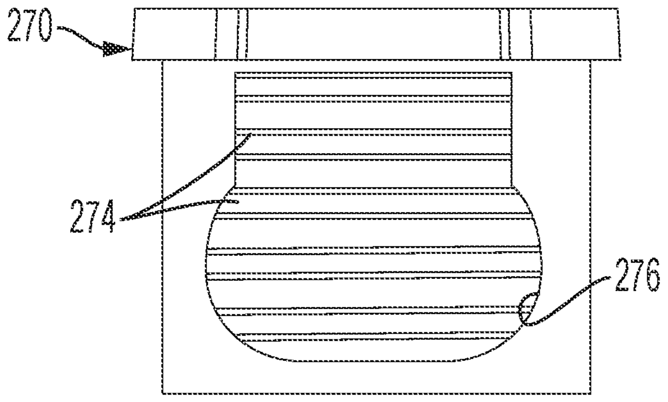
FIG. 23 is view of the gripping insert of FIG. 22 as seen from line 23-23 of FIG. 22.

Referring now to the drawings, FIGS. 1-4 illustrate an implant extractor 100 in accordance with an exemplary embodiment of the present disclosure. The implant extractor 100 comprises a shaft body 102 with a tool connector 104 extending from a proximal end thereof. A push rod 106 is housed within the shaft body 102, extends therefrom, and is movable relative to the shaft body. A proximal end of the push rod is adapted to be received in a through bore 108 (FIG. 6) of the shaft body. A curved jaw support arm 110 extends from the shaft body 102, and a curved jaw 112 is slidable along the curved jaw support arm and movable between a locking position and an unlocking position. In the locking position, the curved jaw 112 engages a trunnion 500 of an implant 502 (FIGS. 18 and 19), and in the unlocking position the curved jaw disengages from the implant trunnion 500.

Figure 5:
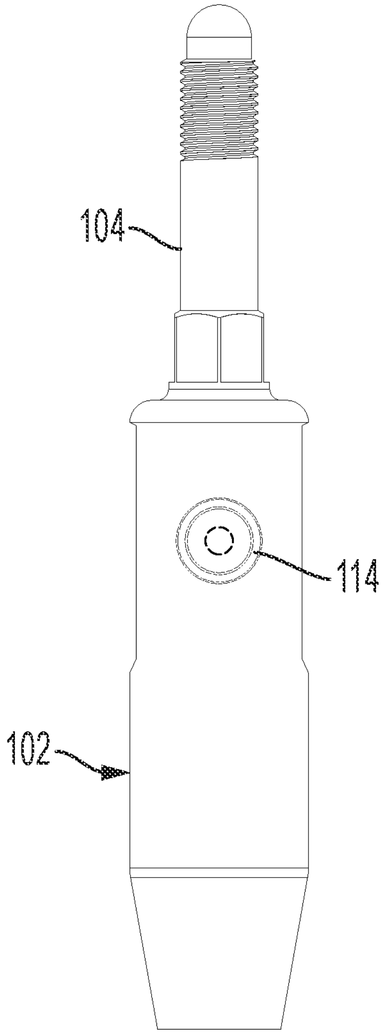
FIG. 5 is a front view of a shaft body of the implant extractor of FIG. 1 with a tool connector extending from a proximal end thereof.
Figure 6:
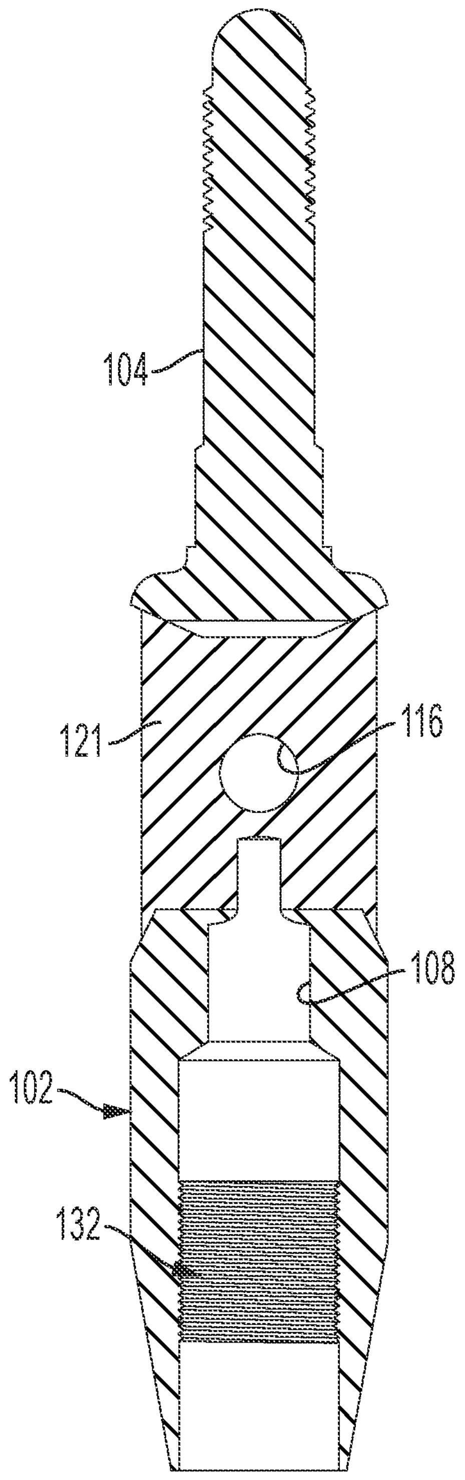
FIG. 6 is a cross-sectional view of the shaft body and tool connector of FIG. 5.
Figure 7:
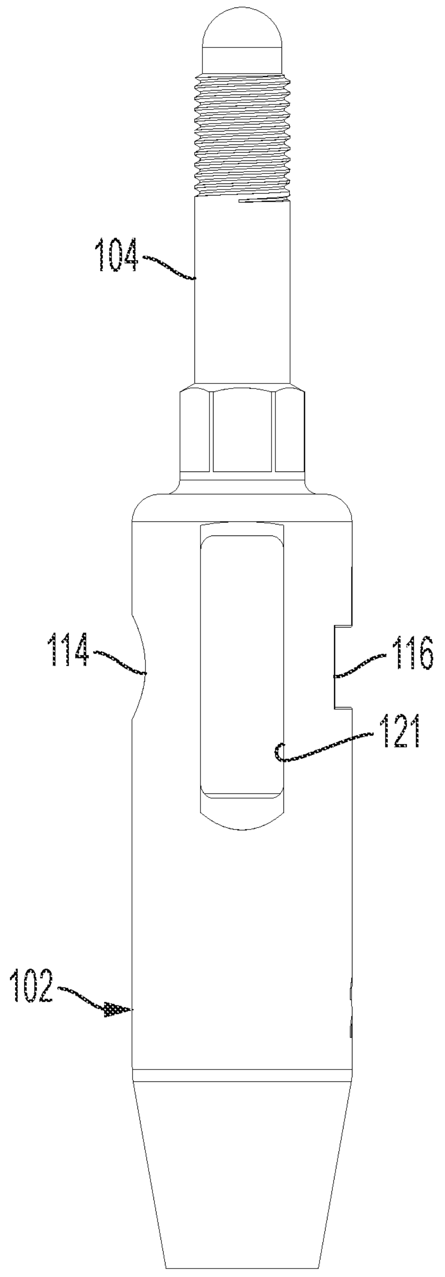
FIG. 7 is a side view of the shaft body and tool connector of FIG. 5.

The shaft body 102 is best shown in FIGS. 5-7. The shaft body includes a tool connector 104 at a proximal end thereof and aligned holes 114, 116 in opposite lateral walls thereof for receiving a fastener 118 (FIG. 1) for pivotably securing a cam lock 120, which is described below in connection with FIGS. 3, 15, 16, 18 and 19, to the shaft body. In this regard, the shaft body 102 includes an anterior to posterior extending slot 121 for receiving a cam 124 of the cam lock 120. In addition, through bore 108 of the shaft body includes an internally threaded distal end 132 (FIG. 6) described in greater detail below.

The tool connector 104 can be integrally or releasably secured to the shaft body 102. The tool connector is adapted for threaded or other secure connection to an unillustrated extraction tool including, without limitation, a T-handle or a C-Frame, which enables a surgeon to exert extraction force on the implant extractor 100 when the implant extractor is engaged with an implant to be extracted. The tool connector can be connected coaxially with the shaft body or inclined at an acute angle relative thereto.

Figure 8:
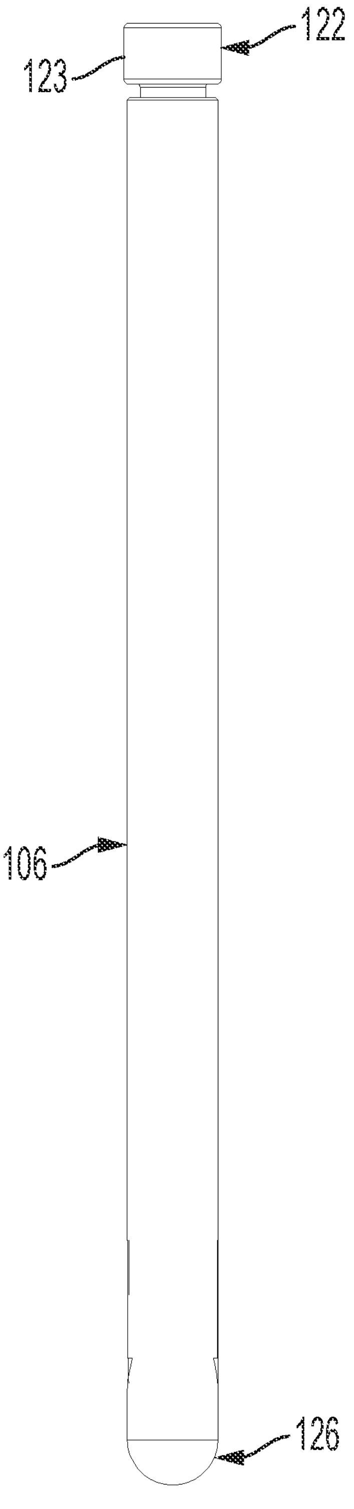
FIG. 8 is a side view of a push rod of the implant extractor of FIG. 1.

The push rod 106 is best illustrated in FIG. 8 and is constructed as a straight, rigid elongate shaft having a proximal end 122 adapted to be engaged by the cam 124 of the cam lock (FIGS. 3, 15, 16, 18 and 19) and a distal end 126 adapted to engage a proximal end 128 of the curved jaw 112 (FIGS. 12, 13 and 17), as described in greater detail below. Preferably, the proximal end 122 of the push rod is provided with a hardened fitting 123 adapted to receive displacement forces exerted by a first portion 156, a second portion 158 and a locking portion 160 of the cam 124 as described below in connection with FIGS. 15 and 16. The push rod can be approximately 12 to 16 cm (including 11.0, 11.5, 12.5, 13.0, 13.5, 14.0, 14.5 15.0, 15.5, 16.5 and 17.0 cm) in length and about 8.5 to 10.5 mm (including 8.0, 9.0, 9.5, 10.0 and 11.0 mm) in diameter.

Figure 4:
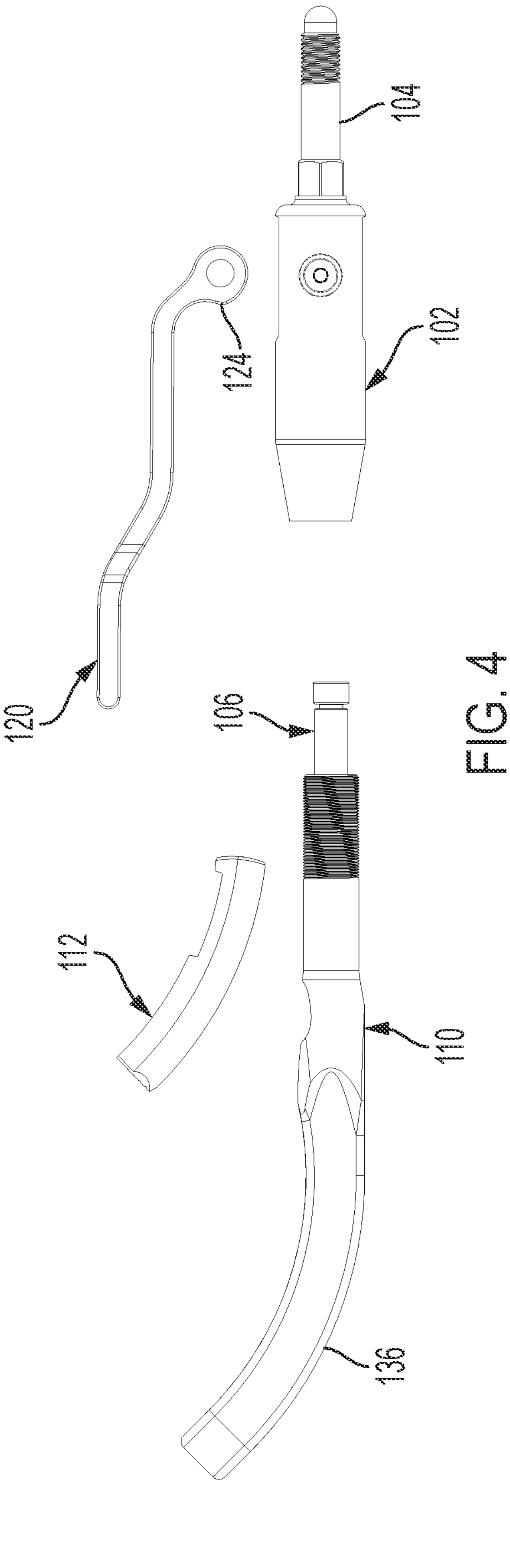
FIG. 4 is an exploded view of the implant extractor of FIG. 1.
Figure 9:
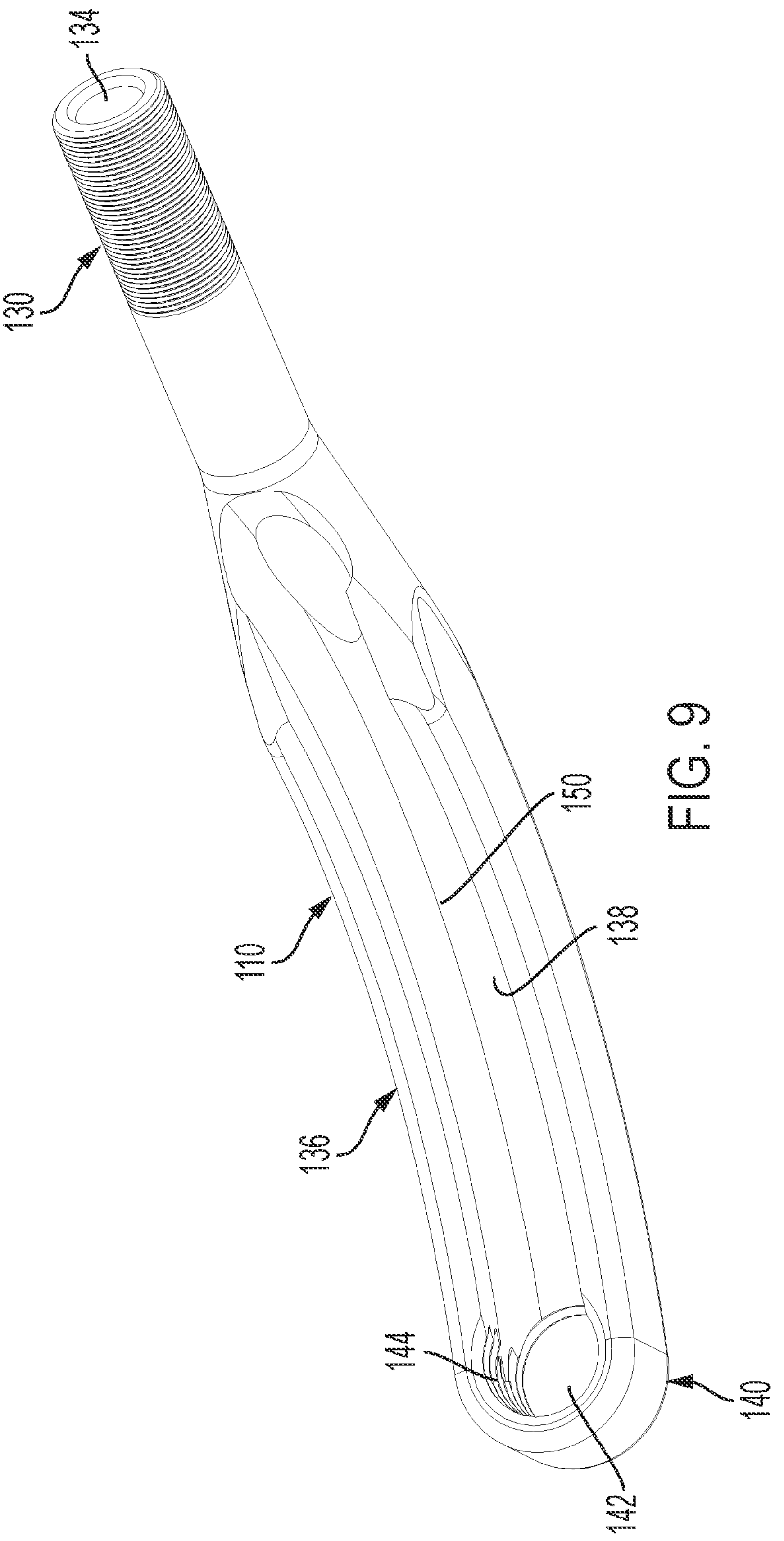
FIG. 9 is a perspective view of a curved jaw support arm of the implant extractor of FIG. 1.
Figure 10:
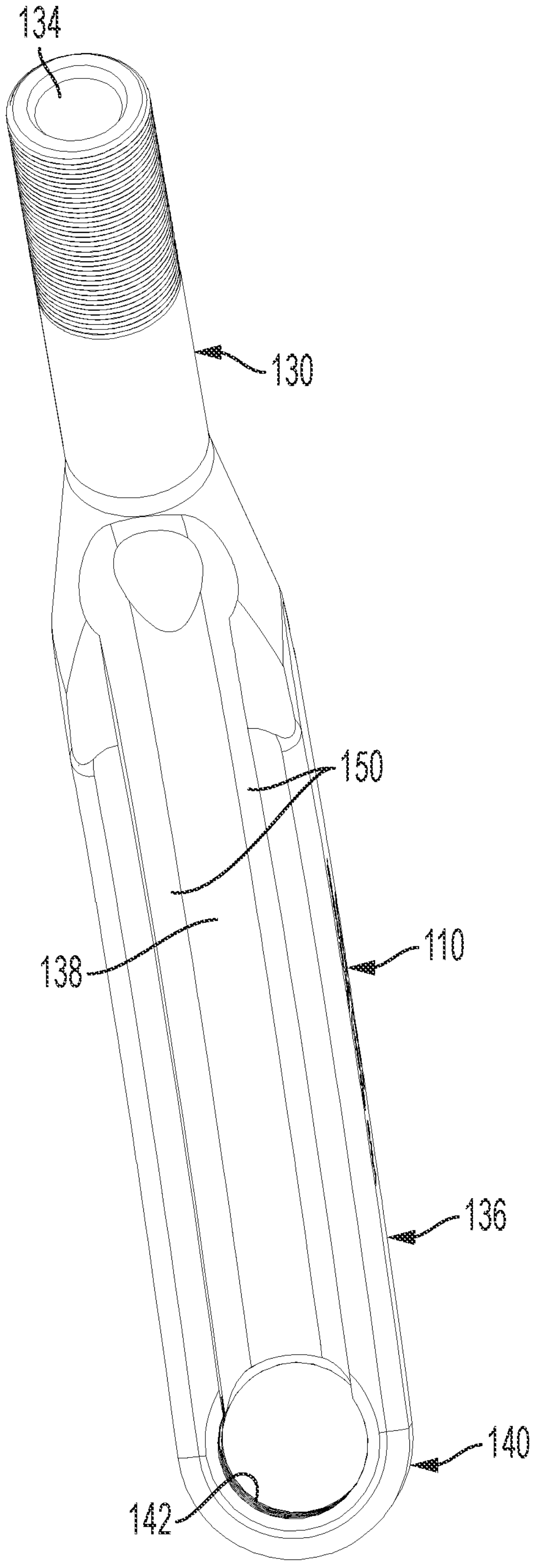
FIG. 10 is a front view of the curved jaw support arm of FIG. 9.
Figure 11:
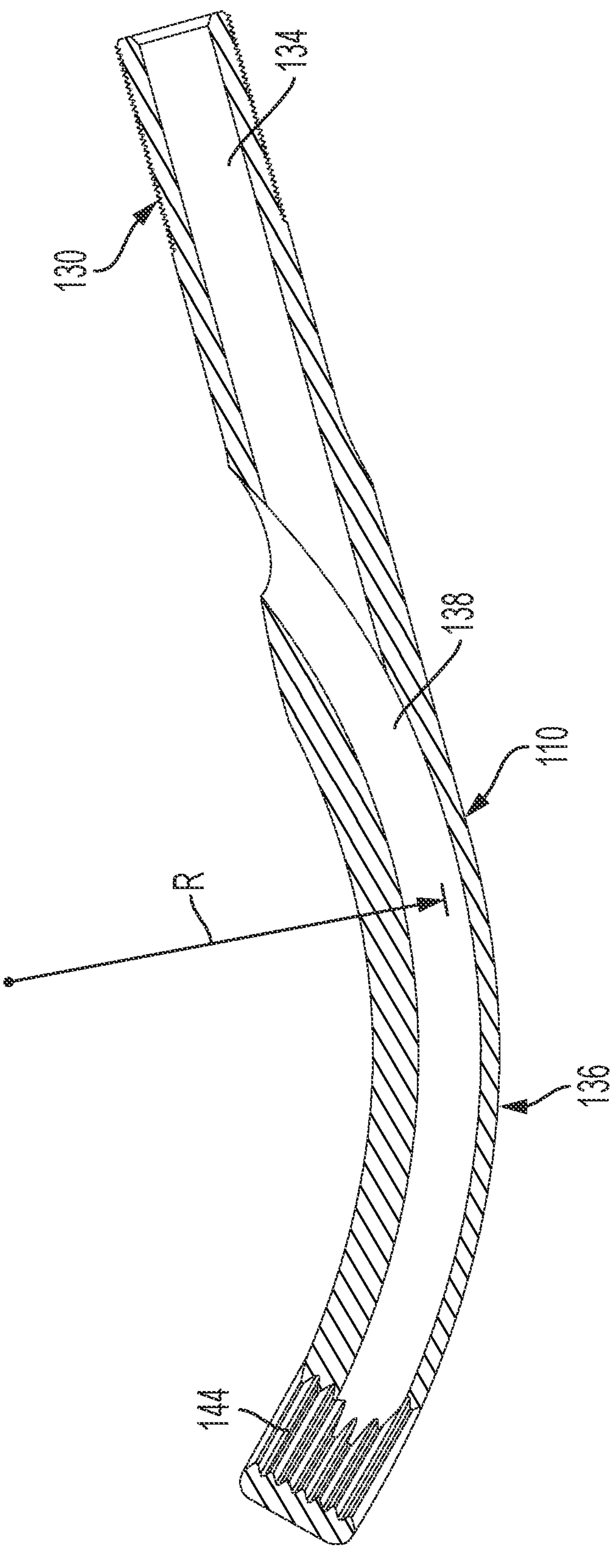
FIG. 11 is a cross-sectional view of the curved jaw support arm of FIG. 9.

FIGS. 9-11 illustrate an exemplary embodiment of the curved jaw support arm 110 constructed in accordance with the subject disclosure. The curved jaw support arm has an externally threaded proximal end 130 configured for threaded connection to the internally threaded distal end 132 of the shaft body 102 (FIG. 6). The externally threaded proximal end includes a through bore 134 sized to slidably receive the push rod 106 as shown in FIG. 4, i.e., the push rod is sized to pass through the through bore 134. The curved jaw support arm has a curved portion 136 with a radius of curvature "R" (FIG. 11) of about 5 cm to 21 cm, including 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.5 and 22.0 cm.

Further, the curved portion has an arc length of between about 6 to 10 cm (including 5.0, 5.5, 6.5, 7.0, 7.5, 8.0. 8.5, 9.0, 9.5, 10.5 cm and 11.0 cm). The curved portion 136 is provided with a curved internal track 138 having a cross-sectional shape configured to slidably and matingly receive the curved jaw 112 (which has a radius of curvature corresponding to or complementary to the radius of curvature of the curved portion 136 of the curved jaw support arm 110). In particular, the curved portion 136 has internal recesses 150 (FIGS. 9 and 10) that cooperate with laterally outwardly protruding walls 148 of the curved jaw 112 (FIGS. 12-14) in a manner to be described below. The overall width and length of the curved portion is such that it allows a line of force of the curved portion to substantially align with the implant 502 (FIGS. 18 and 19) for optimum extraction force exerted on the implant.

A distal end 140 of the curved jaw support arm includes a central passageway 142 having a longitudinal axis "$A_1$" transverse to a longitudinal axis "$A_2$" of the shaft of the through bore 134 and likewise the shaft body 102 (FIG. 1) when assembled thereto. According to an exemplary embodiment, the distal end of 140 of the curved jaw support arm includes grip enhancing structure 144, e.g., a plurality of ridges, teeth, or the like, which cooperate with grip enhancing structure 146, e.g., a plurality of ridges, teeth, or the like, at a distal end of the curved jaw 112 (FIGS. 2, 12-14 and 17) for engaging an implant trunnion, e.g., hip stem implant trunnion 500 (FIGS. 18 and 19), as described below.

Figure 12:
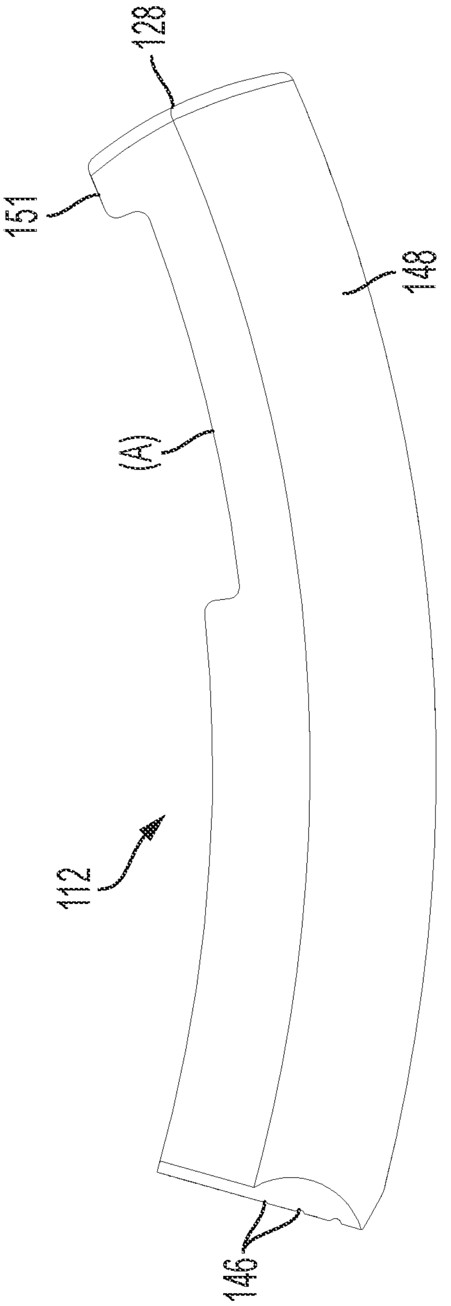
FIG. 12 is a side view of a curved jaw of the implant extractor of FIG. 1.
Figure 13:
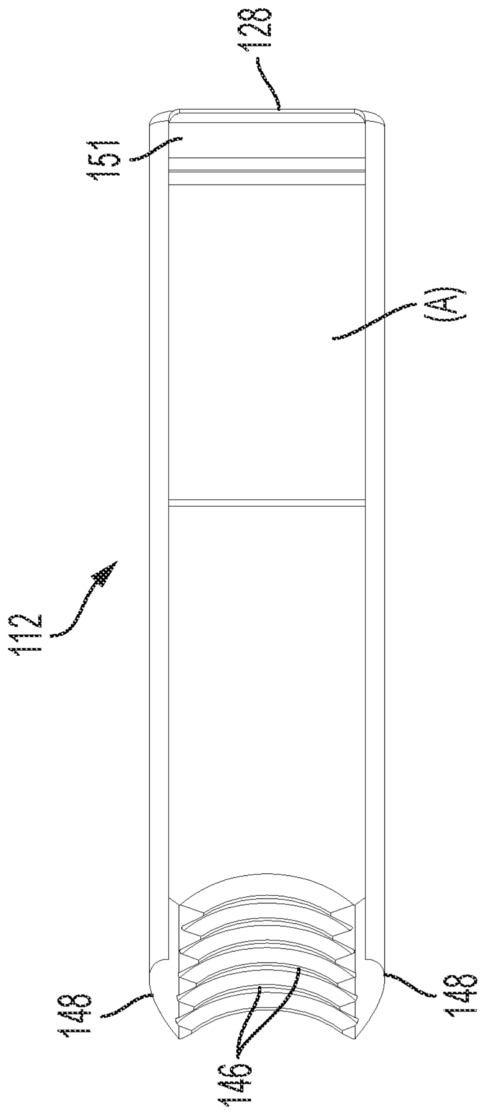
FIG. 13 is a top view of the curved jaw of FIG. 12.
Figure 14:
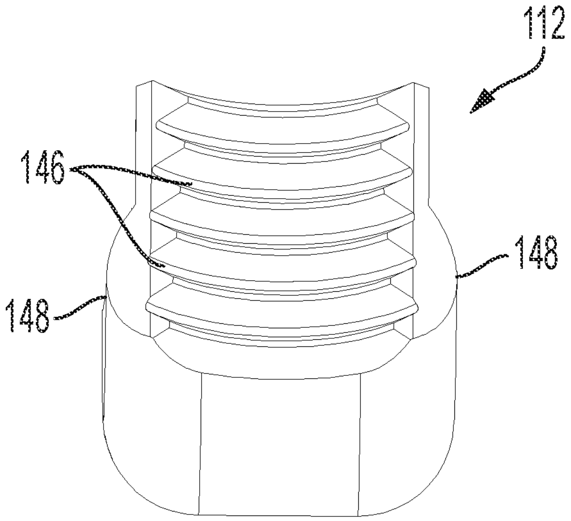
FIG. 14 is a distal end view of the curved jaw of FIG. 12.

The curved jaw 112 is best illustrated in FIGS. 12-14. Along its opposite lateral sides, the curved jaw can be provided with provided with the aforementioned laterally outwardly protruding walls 148 which are configured to be slidably received within correspondingly-shaped recesses 150 (FIGS. 9 and 10) which can be provided along the curved portion 136 of the curved jaw support arm 110. So constructed and arranged, the curved jaw 112 is keyed for slidable movement along the curved jaw support arm, i.e., the curved jaw is securely received within the curved jaw support arm as it slidingly moves therein. In its upper surface, the covered jaw includes a recess "A" having a radius of curvature of about 8 cm to 11 cm (including 7.5, 8.5, 9.0, 9.5, 10.0, 10.5 and 11.5 cm), and an arc length of about 22 mm to about 29 mm (including 21.0, 21.5, 22.5, 23.0, 23.5, 24.0, 24.5, 25.0, 25.5, 26.0, 26.5, 27.0, 27.5, 28.0, 28.5, 29.5 and 30.0 mm). The recess "A" defines an upstanding proximal lip 151 (FIG. 12) that is adapted to be engaged by a user's thumb or other finger to loosen the grip of the of the curved jaw on the implant trunnion once the implant has been extracted from the patient's body, whereby the curved jaw releases the trunnion and thus the implant from the implant extractor 100.

Figure 15:
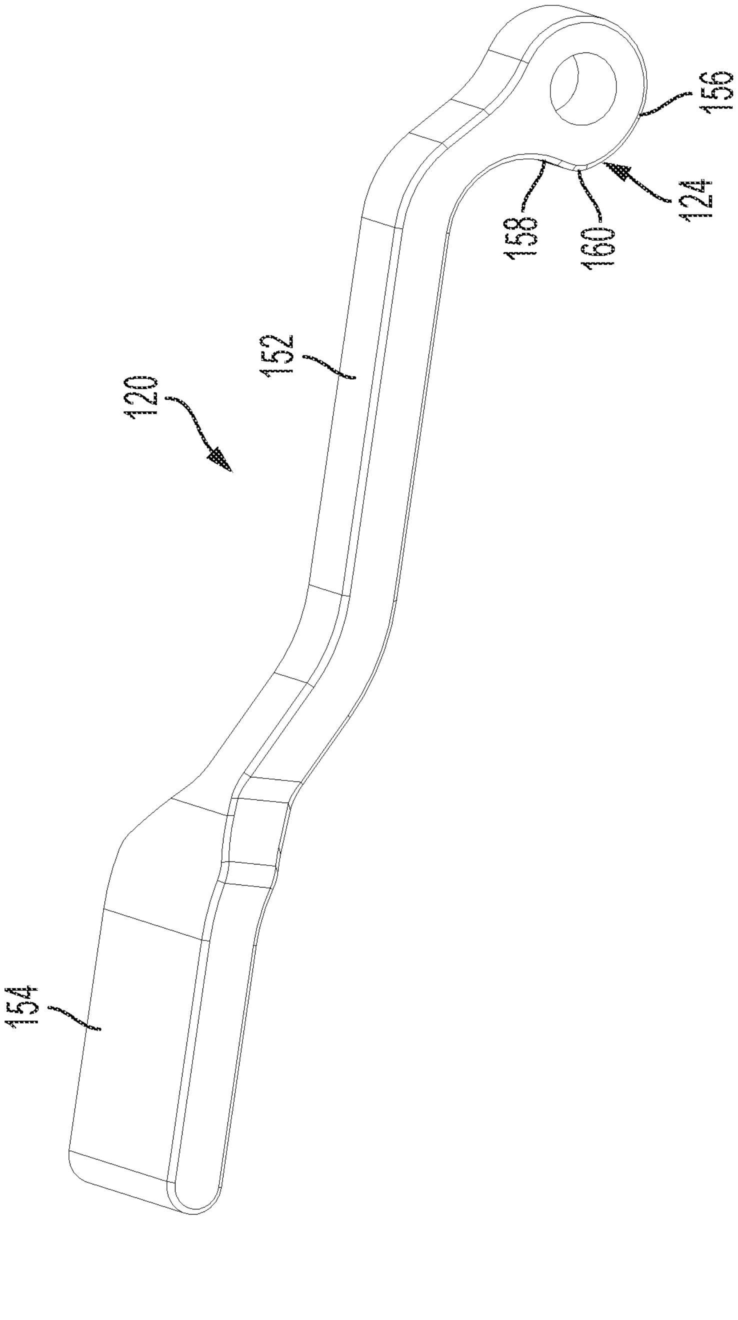
FIG. 15 is a perspective view of a cam lock of the implant extractor of FIG. 1.
Figure 16:
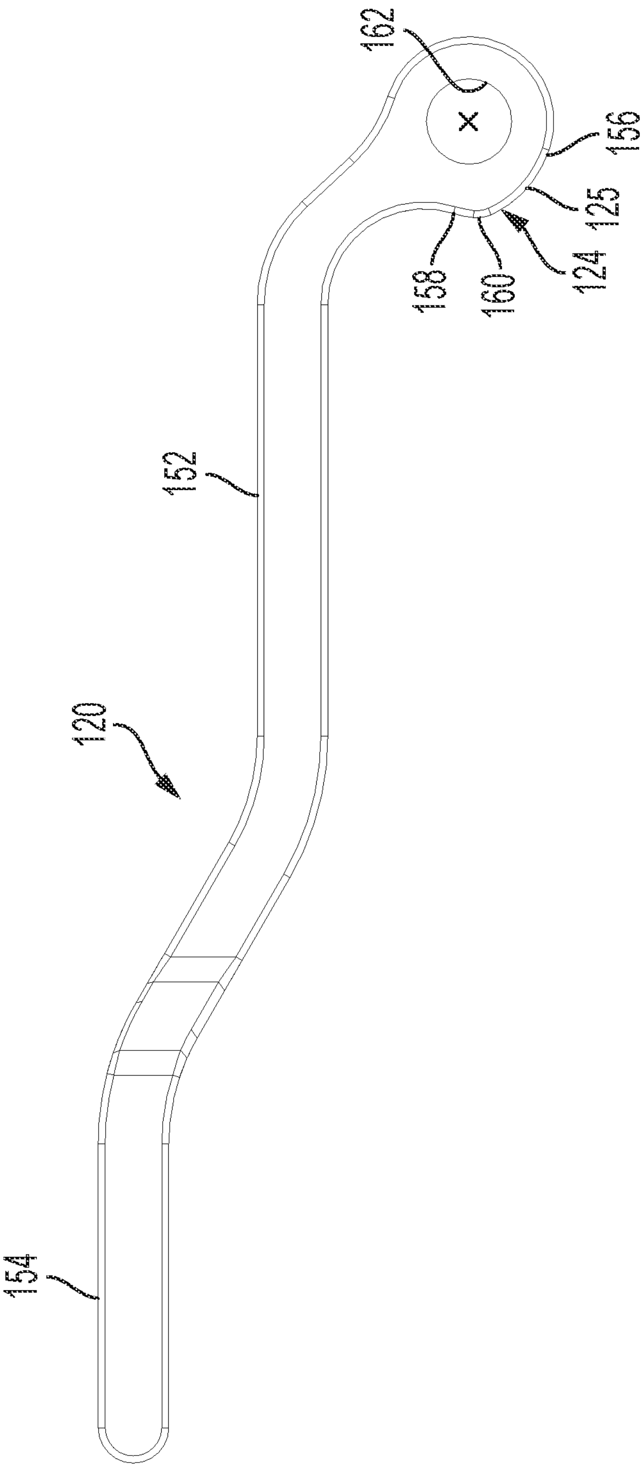
FIG. 16 is a side view of the cam lock of FIG. 15.
Figure 17:
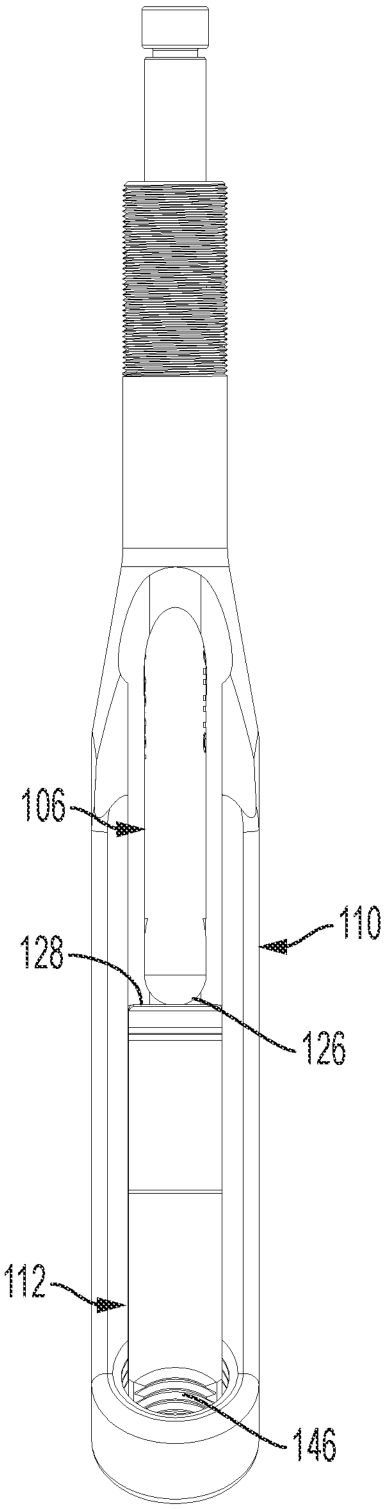
FIG. 17 is a front view of a portion of the implant extractor of FIG. 1.

The cam lock 120 is configured as shown in FIGS. 15 and 16 and is operatively engaged with the push rod 106, in particular the proximal end 122 thereof. The cam lock 120 includes the cam 124 and a lever 152 extending from the cam to a paddle-shaped grip portion 154. The cam 124 is housed within the shaft body 102 and is pivotably connected thereto by the fastener 118.

As best illustrated in FIGS. 15 and 16, the cam 124 has a continuously curved cam surface throughout its range of motion. In particular, the continuously curved cam surface includes a first portion 156 with a continuously increasing radius of curvature contiguous with a second portion 158 with a continuously decreasing radius of curvature, wherein a juncture of the first portion and the second portion defines a locking portion 160 of the continuously curved cam surface. According to an aspect, the first portion 156 and the second portion 158 are each convex in shape. According to another aspect, the locking portion 160 is convex in shape and has no V-shaped or other ridge-shaped profile. According to an exemplary, although non-limitative embodiment, the first portion 156 has a minimum radius of about 7.6 mm (0.3005 inches) as measured from the center "X" of a fastener through hole 162 (FIG. 16) that continuously increases toward the locking portion 160 to a maximum radius of about 8.7 mm (0.342 inches), the second portion 158 has a maximum radius of about 8.7 mm (0.342 inches) that continuously decreases from the locking portion 160 to a minimum radius of 8.4 mm (0.330 inches), and the locking portion has a substantially constant radius of about 8.7 mm (0.342 inches) spanning an arc length of about 1.6 mm (0.064 inches).

The continuously curved cam surface of the cam 124 avoids the "jerking" one feels when opening and closing conventional cam locks which have a V-shaped or other ridge-shaped profile at the peak of the cam surface. Additionally, it has been observed that the continuously curved cam surface of the cam 124 results in at least a 60% increase in clamping pressure and at least a 45% decrease in release force versus conventional cam handles which have a ridge or V-shaped profile at the peak of the cam surface. For example, it has been observed that when using a conventional cam handle having a ridge or V-shaped profile at the peak of the cam surface, the maximum clamping pressure exerted by such a cam is approximately 25,000,000 to 28,000,000 newtons/$m^2$ (800-900 pounds applied over a contact area of 0.22 square inches (i.e., the contact area of the peak of the cam on the hardened fitting 123 at the proximal end 122 of the push rod 106)) and the release force is approximately 160 newtons (36 pounds). In contrast, it has been observed that when using the present cam handle having a continuously curved cam surface, the maximum clamping force exerted by such a cam is approximately 45,000,000 newtons/$m^2$ (1500 pounds applied over a contact area of 0.22 square inches (i.e., the contact area of the locking portion 160 of the cam on the hardened fitting 123 at the proximal end 122 of the push rod 106)) and the release force is approximately 90 newtons (20 pounds). In addition, a generally paddle-shaped grip portion 154 of the cam lock 120 is more than 50% larger in surface area than corresponding grip portions of conventional cam handles, thereby reducing pressure on the hand and rendering operation of the hip stem implant extractor 100 more comfortable during use.

FIGS. 20-23 show the construction of another exemplary embodiment of an implant extractor in accordance with the subject disclosure. In many respects, the implant extractor 200 is constructed and functions substantially similarly to the implant extractor 100 described above. Accordingly, for brevity, only those features of the implant extractor 200 which materially depart in structure and/or function from those of the implant extractor 100 will be described in detail.

Referring to FIGS. 20-23, a distinction between the implant extractor 200 and the implant extractor 100 is that the implant extractor 200 further comprises a replaceable gripping insert 270 received within a central passageway 272 at the distal end of the curved jaw support arm 210. The gripping insert includes grip enhancing structure 274 which can be, e.g., a plurality of ridges, teeth, or the like, that aligns with the curved jaw 212 when the gripping insert is received within the central passageway 272. According to an aspect, the curved jaw 212 can be provided with grip enhancing structure 246, e.g., a plurality of ridges, teeth, or the like, that aligns with the grip enhancing structure 274 of the gripping insert. The gripping insert 270 is annular with a lateral opening 276 for receiving the curved jaw 212 therethrough.

Referring back to FIGS. 18 and 19, when the cam lock 120 is in the unlocked position of FIG. 18, the trunnion 500 of the implant 502, e.g., hip stem implant, is first inserted between the opposed gripping enhancing structures of either type described above. The cam lock is then moved or pivoted downwardly to the locked position of FIG. 19, whereby the locking portion 160 of the cam 124 pushes the push rod 106 against the proximal end of the curved jaw 112 (or 212), whereby the opposed gripping enhancing structures firmly grip the trunnion 500. With the implant extractor so configured, an extraction tool may be connected to the threaded tool connector 104 and may be used to exert an extraction or pulling force on the implant extractor to extract the implant 502 from a patient's hip or other bone.

A typical anterior hip stem implant extractor tool has a longitudinal axis generally coextensive with the hip stem implant to be extracted. As a result, this allows the device to clear the patient's body which is necessary due to the typical orientation the patient's body needs to be placed in to perform the surgery via the direct anterior approach. In this approach, the incision is made on the anterior plane of the hip which differs from the posterior-lateral approach. Thus, in order to align the hip stem with an opening for extraction, the patient's leg needs to be dislocated and bent posterior or to the rear to allow access. Otherwise, the patient's mid-section would prevent the hip stem from being extracted. The patient's leg can only be positioned to such a maximum angle dependent on the patient's anatomy, thus the necessary surgical instrumentation to remove a patient's hip stem requires an offset to clear the patient's belly. Such an offset is not needed for a posterior lateral approach because the patient can easily be bent forward at the hip in a regular anatomical position and have the hip stem extracted posteriorly, i.e., out the rear. The direct anterior approach is gaining popularity because significantly less soft tissue needs to be severed to allow for the surgery when compared to the posterior-lateral approach, which in turn, allows for considerable reduction in recovery time for the patient. Indeed, in some cases the anterior approach allows patients to be walking on their own the day after surgery.

The subject disclosure, in contrast, provides an implant extractor which functions as an effective tool for achieving direct anterior hip stem implant extraction and the aforementioned benefits associated therewith.

It will be appreciated by those skilled in the art that changes could be made to the exemplary embodiments described above without departing from the broad inventive concept thereof. It is to be understood, therefore, that this disclosure is not limited to the particular exemplary embodiments disclosed, but it is intended to cover modifications within the spirit and scope of the subject disclosure as defined by the appended claims.

We claim:

1. An implant extractor comprising:
- a shaft body;
- a push rod extending from the shaft body;
- a curved jaw support arm extending from the shaft body, wherein a distal end of the curved jaw support arm includes a central passageway having a longitudinal axis transverse to a longitudinal axis of the shaft body;
- a curved jaw slidable along the curved jaw support arm and movable between a locking position and an unlocking position; and
- a gripping insert received within the central passageway, wherein the gripping insert is annular with a lateral opening receiving the curved jaw.

2. The implant extractor of claim 1, further comprising a cam lock operatively engaged with the push rod.

3. The implant extractor of claim 2, wherein the cam lock includes a cam housed within the shaft body, and a lever extending from the cam.

4. The implant extractor of claim 2, wherein the cam lock includes a cam having a continuously curved cam surface throughout its range of motion.

5. The implant extractor of claim 1, wherein the push rod is housed within the shaft body.

6. The implant extractor of claim 1, wherein a distal end of the push rod engages a proximal end of the curved jaw.

7. The implant extractor of claim 1, wherein the push rod is movable relative to the shaft body.

8. The implant extractor of claim 1, wherein the curved jaw support arm has a curved portion with a radius of curvature of about 5 to 21 mm.

9. The implant extractor of claim 1, wherein the gripping insert includes grip enhancing structure that aligns with the curved jaw when the gripping insert is received within the central passageway.

10. The implant extractor of claim 1, further comprising a tool connector extending from a proximal end of the shaft body.

11. An implant extractor comprising:
- a shaft body;
- a tool connector extending from a proximal end of the shaft body;
- a push rod mounted within and slidable within the shaft body;
- a cam lock mounted within the shaft body for engaging a proximal end of the push rod;
- a curved jaw support arm extending from the shaft body, wherein a distal end of the curved jaw support arm includes a central passageway having a longitudinal axis transverse to a longitudinal axis of the shaft body;
- a curved jaw slidably received in the curved jaw support arm and movable between a locking position and an unlocking position; and
- a gripping insert received within the central passageway, wherein the gripping insert is annular with a lateral opening receiving the curved jaw.

12. The implant extractor of claim 11, wherein the cam lock includes a cam having a continuously curved cam surface throughout its range of motion.

13. The implant extractor of claim 12, wherein the continuously curved cam surface includes a first portion with a continuously increasing radius of curvature contiguous with a second portion with a continuously decreasing radius of curvature, wherein a juncture of the first portion and the second portion defines a locking portion of the continuously curved cam surface.

14. The implant extractor of claim 13, wherein first portion and the second portion are each convex in shape.

15. The implant extractor of claim 13, wherein locking portion is convex in shape.

16. The implant extractor of claim 13, wherein locking portion has no ridge-shaped profile.

* * * * *